(12) United States Patent
Oskin et al.

(10) Patent No.: US 8,597,305 B2
(45) Date of Patent: Dec. 3, 2013

(54) TENACULUM STABILIZER DEVICE

(75) Inventors: Christopher Oskin, Grafton, MA (US);
Brian MacLean, Westford, MA (US);
Stephen Keaney, Groton, MA (US);
Jozef Slanda, Milford, MA (US);
Jeffrey Zerfas, Bloomington, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 804 days.

(21) Appl. No.: 12/207,931

(22) Filed: Sep. 10, 2008

(65) Prior Publication Data
US 2009/0112227 A1 Apr. 30, 2009

Related U.S. Application Data

(60) Provisional application No. 60/971,409, filed on Sep. 11, 2007.

(51) Int. Cl.
*A61B 17/42* (2006.01)
(52) U.S. Cl.
USPC ........................................................ 606/119
(58) Field of Classification Search
USPC ......... 606/119–128, 110, 108, 205, 208, 193,
606/198, 191, 194, 192, 167, 170, 171, 157,
606/158, 206, 207, 209, 210, 190, 130;
600/121, 124, 125, 131, 204, 202, 210,
600/235, 201, 156, 570, 578, 562, 215–221,
600/227, 226, 207; 604/95.01, 95.04, 515,
604/540, 528, 275, 171, 104, 248, 278, 27;
623/23.66
See application file for complete search history.

(56) References Cited

U.S. PATENT DOCUMENTS

| | | | | |
|---|---|---|---|---|
| 2,707,957 | A * | 5/1955 | Sollmann | 604/264 |
| 3,777,743 | A * | 12/1973 | Binard et al. | 600/562 |
| 3,796,211 | A * | 3/1974 | Kohl | 600/562 |
| 4,000,743 | A * | 1/1977 | Weaver | 606/119 |
| 4,611,888 | A * | 9/1986 | Prenovitz et al. | 600/112 |
| 4,702,252 | A * | 10/1987 | Brooks et al. | 606/195 |
| 5,195,964 | A * | 3/1993 | Kletzky et al. | 604/523 |
| 5,368,598 | A * | 11/1994 | Hasson | 606/119 |
| 5,441,044 | A * | 8/1995 | Tovey et al. | 600/234 |
| 5,498,230 | A * | 3/1996 | Adair | 600/112 |
| 5,935,098 | A * | 8/1999 | Blaisdell et al. | 604/515 |
| 6,899,717 | B2 * | 5/2005 | Weber et al. | 606/107 |
| 2002/0120180 | A1 * | 8/2002 | Speier et al. | 600/125 |
| 2003/0028196 | A1 * | 2/2003 | Bonutti | 606/87 |
| 2004/0097961 | A1 * | 5/2004 | Burbank et al. | 606/119 |
| 2004/0127931 | A1 | 7/2004 | Kincaid et al. | |

FOREIGN PATENT DOCUMENTS

| | | |
|---|---|---|
| EP | 0 642 766 | 3/1995 |
| WO | 01/52716 | 7/2001 |

* cited by examiner

*Primary Examiner* — Thomas McEvoy
*Assistant Examiner* — Jocelin Tanner
(74) *Attorney, Agent, or Firm* — Fay Kaplun & Marcin, LLP

(57) ABSTRACT

An apparatus for treating tissue, comprising a sheath defining a lumen sized and shaped to receive a treatment device therein, a guide member coupled to the sheath and extending a predetermined distance substantially parallel to a longitudinal axis of the sheath, and a stabilizer element for engaging an anchoring device coupled to tissue to stabilize the sheath and the treatment device, the stabilizing element being movably coupled to the guide member for movement therealong substantially parallel to the longitudinal axis of the sheath wherein, when in a proximal-most position, the stabilizer element is located proximally of a proximal end of the guide member.

14 Claims, 4 Drawing Sheets

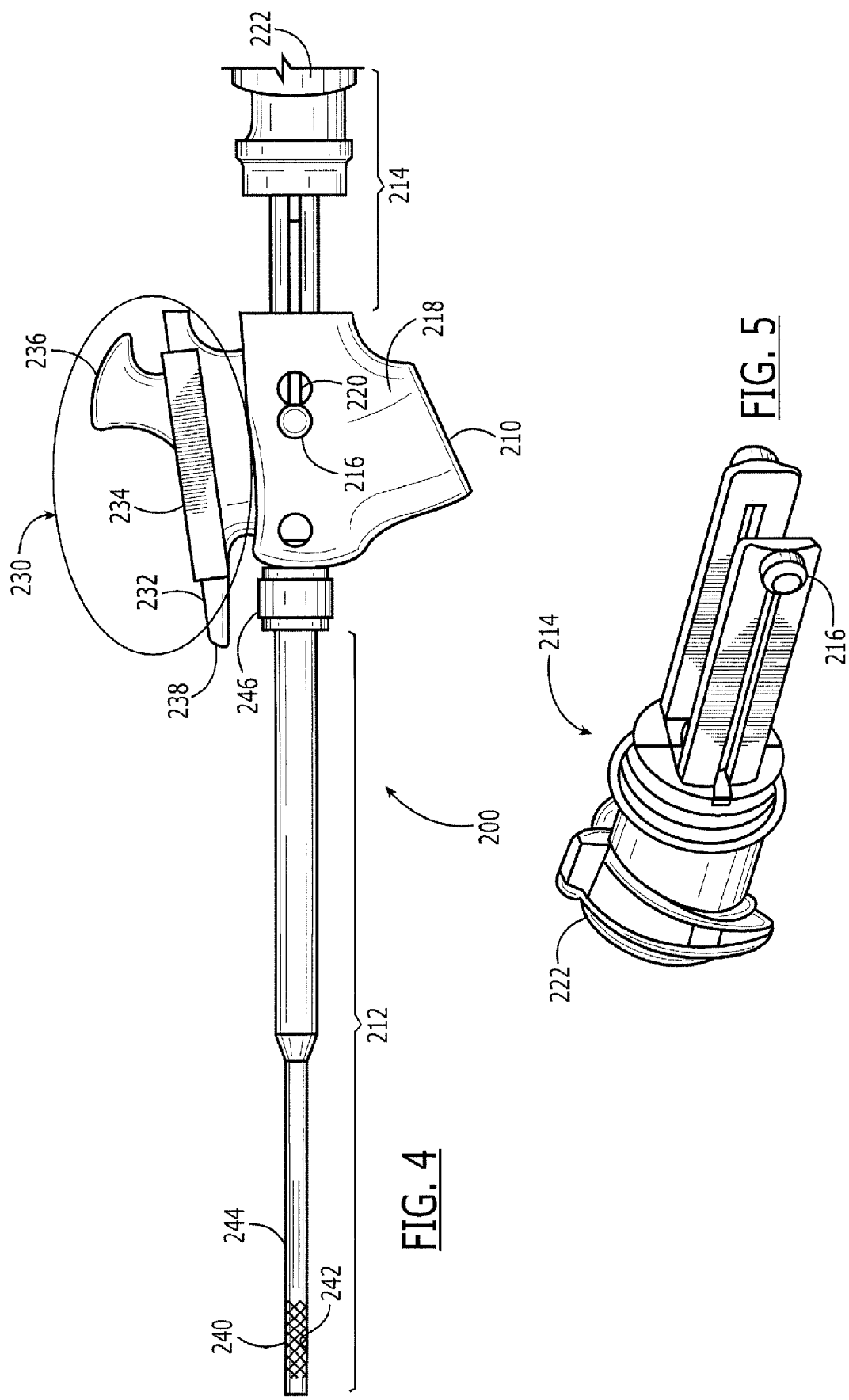

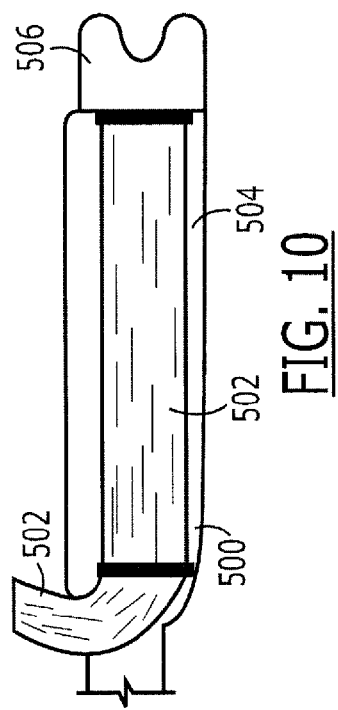
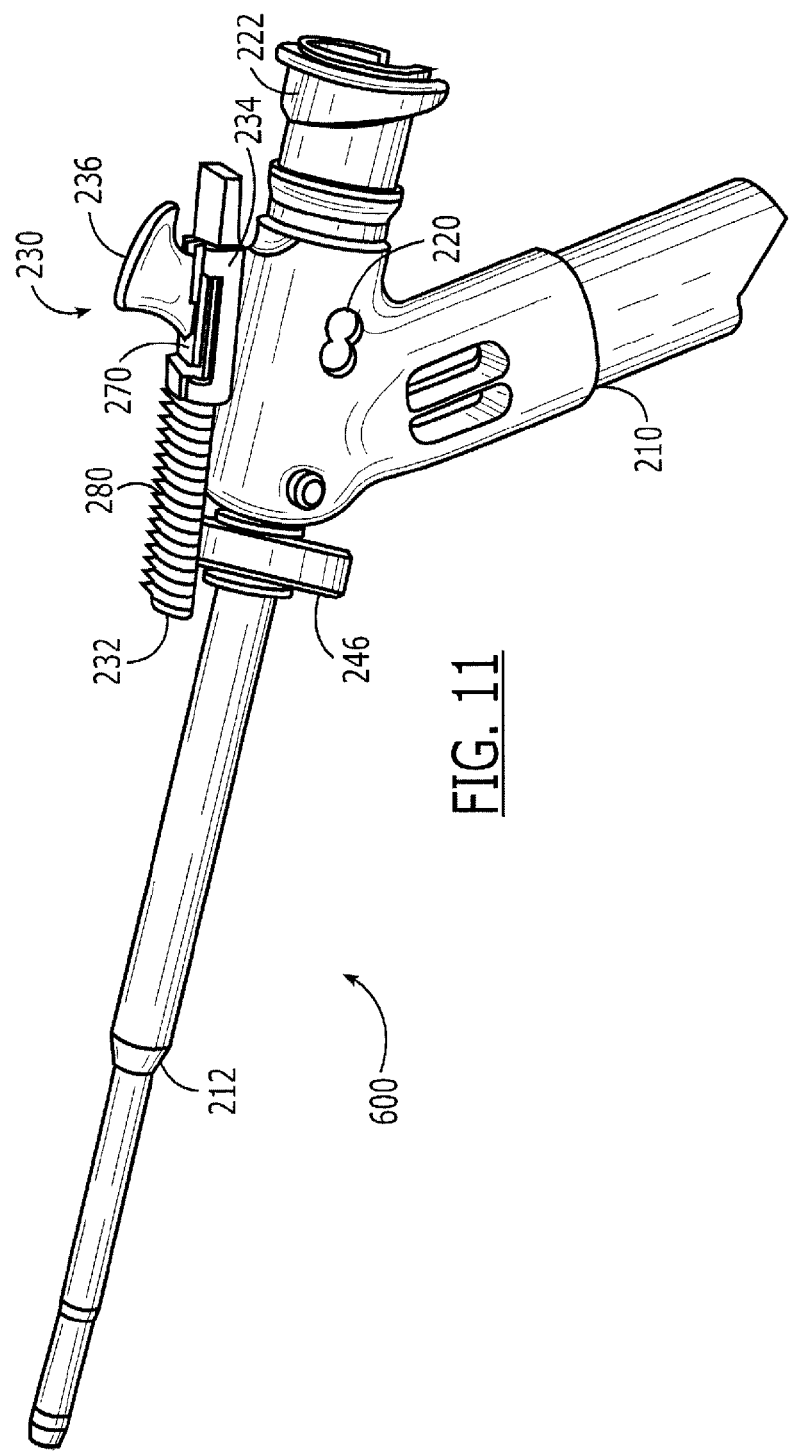

FIG. 11 shows a tenaculum stabilizer arrangement according to a still further embodiment of the invention.

TENACULUM STABILIZER DEVICE

PRIORITY CLAIM

This application claims priority to U.S. Provisional Application Ser. No. 60/971,409, entitled "Tenaculum Stabilizer Device," filed Sep. 11, 2007. The entire disclosure of the above-identified application is incorporated herewith by reference into this application.

BACKGROUND INFORMATION

During procedures that require the insertion of a device through the cervix into the uterus, it may be necessary to seal the cervical opening to prevent fluids, gases etc. introduced into the uterus from escaping into the vagina. If such a device is prematurely withdrawn from the uterus (i.e., if a distal tip of the device is moved proximally beyond the cervical os), fluids and/or gases may be introduced into the vagina. Thus a tenaculum may be used to lock the device in place and prevent such premature withdrawal.

For example, if the lining of the uterus is to be ablated using heated fluids inserted into the uterus via a device inserted through the cervix, it is important to prevent the heated fluids from damaging vaginal tissue. An exemplary system for such treatment is the Hydro ThermAblator® system (HTA) manufactured by the Boston Scientific Corporation.

SUMMARY OF INVENTION

This application relates to an apparatus for treating tissue, comprising a sheath defining a lumen sized and shaped to receive a treatment device therein. A guide member is coupled to the sheath and extends a predetermined distance substantially parallel to a longitudinal axis of the sheath. A stabilizer element for engaging an anchoring device of the apparatus of the present invention is coupled to tissue to stabilize the sheath and the treatment device, the stabilizing element being movably coupled to the guide member for movement therealong substantially parallel to the longitudinal axis of the sheath wherein, when in a proximal-most position, the stabilizer element is located proximally of a proximal end of the guide member.

BRIEF DESCRIPTION OF DRAWINGS

FIG. 4 shows a side view of a hydro thermal ablation system including a tenaculum stabilizer according to a further embodiment of the invention;

FIG. 5 shows a perspective view of a scope adapter for use with the system of FIG. 4;

FIG. 10 shows a tenaculum stabilizer arrangement according to a still further embodiment of the invention; and FIG. 11 shows a tenaculum stabilizer arrangement according to a still further embodiment of the invention.

DETAILED DESCRIPTION

Figure 1:
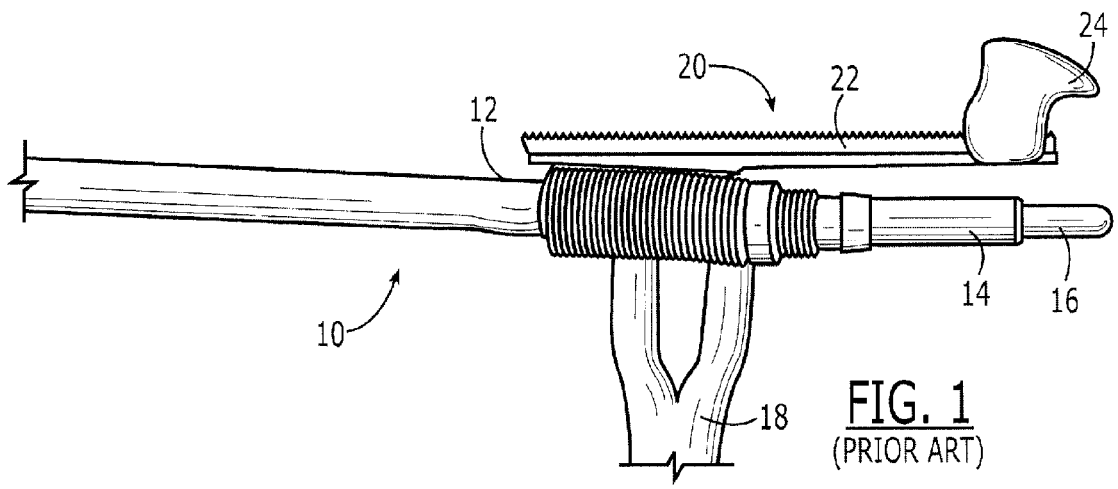
FIG. 1 shows a side view of a conventional tenaculum stabilizer.

The present invention may be further understood with reference to the following description and to the appended drawings, wherein like elements are referred to with the same reference numerals. The present invention relates to devices for stabilizing surgical instruments and, more specifically, relates to devices for stabilizing a tenaculum during procedures within the uterus.

After the distal tip of a sheath of a system such as the HTA system has been inserted into the uterus via the cervix, one or more tenaculums may be employed to enhance the cervical seal to prevent heated liquids from leaking out of the uterus and damaging non-targeted tissue (e.g., vaginal tissue). A tenaculum stabilizer allows the tenaculum to be used to stabilize the sheath by countering forces applied thereto as instruments are inserted through the sheath. This reduces the likelihood that the sheath will be inadvertently pulled out of the cervix. According to the exemplary embodiments of the invention, a novel stabilizer for the tenaculum is provided to further aid in stabilizing the sheath within the cervix while minimizing interference between the stabilizer and the proximal end of a hysteroscope inserted through the sheath.

As will be described in more detail below, a tenaculum stabilizer 100 according to an exemplary embodiment of the invention is designed to work in conjunction with an HTA system or, as would be understood by those of skill in the art, any of a variety of different devices for a wide range of procedures. For example, a tenaculum stabilizer according to the present invention is useful for any procedure in which a device must be inserted into any body cavity and for which it is desired to prevent the premature withdrawal of the device therefrom. Such procedures include, among others, all ablation procedures such as cryogenic, thermal and chemical ablation systems. The tenaculum stabilizer 100 is compatible with currently used tenaculums and, in particular, with those having a length of between about 22.86 and 25.4 cm. as are commonly used in HTA system procedures. As described below, the stabilizer 100 may preferably be made compatible with a wide range of hysteroscopes such as those manufactured by Olympus, Wolfe, ACMI, Karl Storz, etc. which are of different lengths and diameters. As would be understood by those skilled in the art, when a scope is inserted to a desired position within the uterus, the length of the scope extending proximally from the sheath will vary depending on the total length of the scope. The shorter the scope is, the closer the proximal handle of the scope will be to the proximal end of the sheath. The position of the tenaculum stabilizer is then adjusted to lock it against a cross bar or within a thumb loop of the tenaculum to immobilize the sheath relative to the tenaculum.

In contrast, FIG. 1 shows a conventional HTA system 10, including an insertion sheath 12 extending from a proximal scope insertion end 14, to a distal end (not shown) which is inserted into the uterus via the cervix. Those skilled in the art will understand that a cap 16 is removed from the scope insertion end 14 and a hysteroscope (not shown) is inserted through the sheath 12 until a distal end of the scope extends into the uterus for supply and withdraw ablation fluids. The HTA system 10 further includes an inflow/outflow tubing 18 and a tenaculum stabilizer arrangement 20 mounted thereon. The tenaculum stabilizer arrangement 20 includes a guide member 22 mounted on the sheath 12 adjacent to the inflow/outflow tubing 18 and a stabilizer element 24 slidably mounted on the guide member 22. In this embodiment, the guide member 22 forms a track on which the stabilizer element 24 slides to allow for adjustments in the position of the stabilizer element 24 relative to a part of the tenaculum against which the stabilizer element 24 is to be locked to prevent the sheath 12 and the hysteroscope from being inadvertently withdrawn from the uterus. As would be understood by those skilled in the art, the stabilizer element 24 is slidable back and forth over guide member 22 to permit adjustment of the stabilizer arrangement 20 to allow for different tenaculum lengths and tensions. In order to account for the varying position of the feature of the tenaculum against which the stabilizer element 24 is to be locked and/or varying tensions to be applied thereto, the track of the guide member 22 is approximately 9.35 cm. long to allow for a total range of motion of the stabilizer element 24 of 3.38 cm. Thus, the entire range of motion of the stabilizer element 24 is accounted for by the length of the guide member 22. However, as the length of the portion of the scope within the sheath 12 is constant, the portion of the scope extending from the proximal scope insertion end 14 of the sheath 12 varies depending on the length of the scope with control handles of shorter scopes remaining closer to the scope insertion end 14 than control handles of longer scopes. The control handle portions of these scopes are wider than the insertion portions, extending radially outward, in some cases, as far as a radially inner surface of the guide member 22. Thus, for shorter scopes, the control handle will be closer to the scope insertion end 14 and, consequently, to the guide member 22. This may result in the rotation of the scope being interfered with or prevented by the portion P of the guide member 22 extending proximally of the scope insertion end 14 of the sheath 12.

As shown in FIGS. 2-5, a novel HTA system 100 includes a tenaculum stabilizer arrangement 102 according to the invention. The stabilizer arrangement 102 comprises a fin-shaped stabilizer element 104. However, those skilled in the art will understand that other shapes may be used. For example, the stabilizer element 104 may be hook shaped or grooved, or may have any other shape that facilitates attachment to a cross bar, finger loop or body of a tenaculum.

Figure 6:
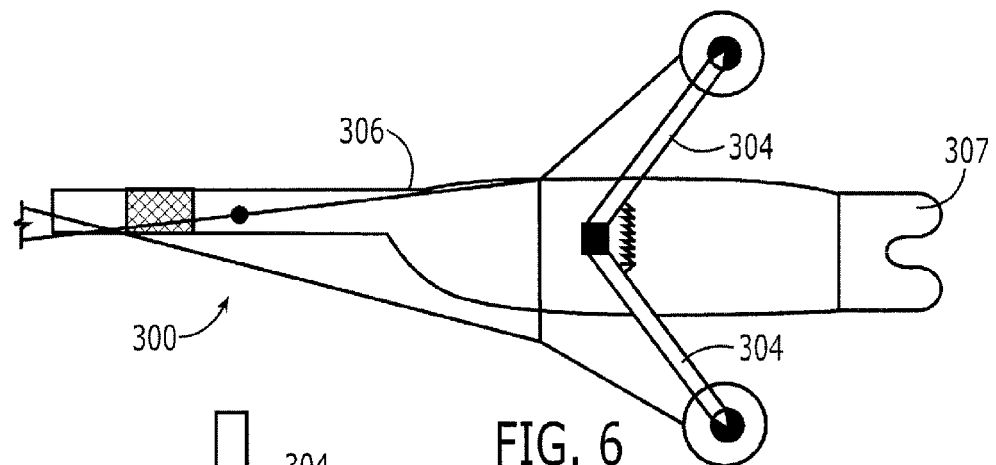
FIG. 6 shows a tenaculum stabilizer arrangement according to an alternate embodiment of the invention.
Figure 7:
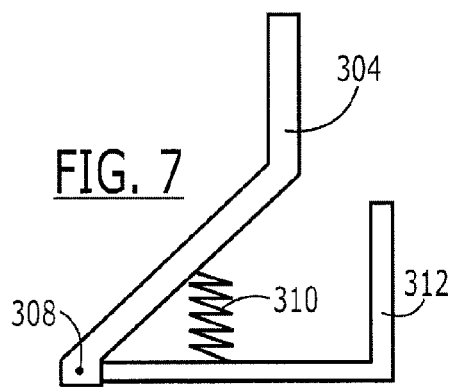
FIG. 7 shows a side view of the tenaculum stabilizer arrangement of FIG. 6.
Figure 8:
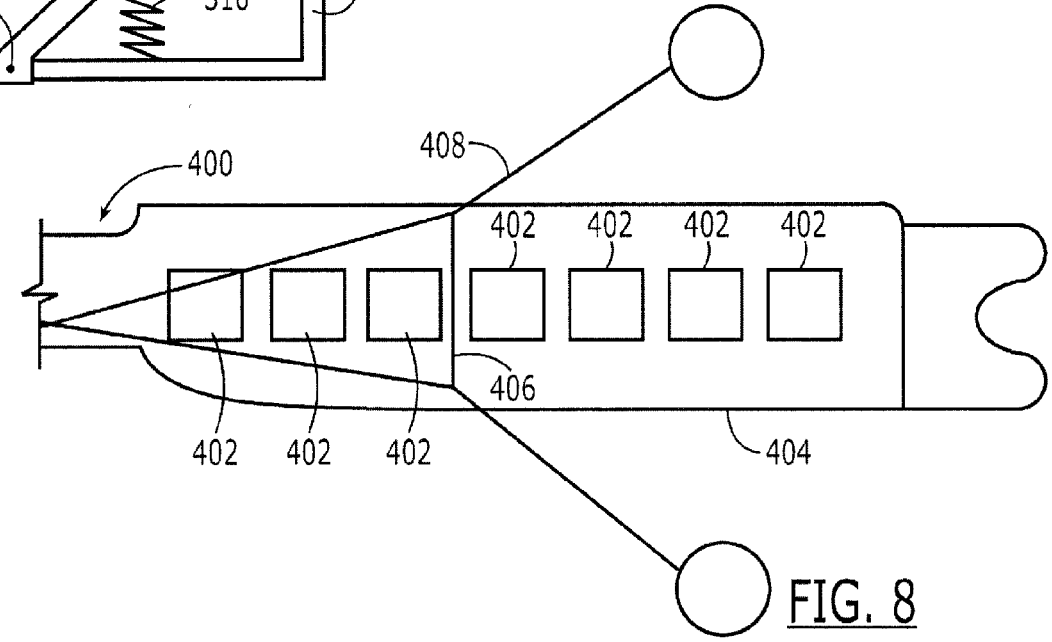
FIG. 8 shows a tenaculum stabilizer arrangement according to a further embodiment of the invention.
Figure 9:
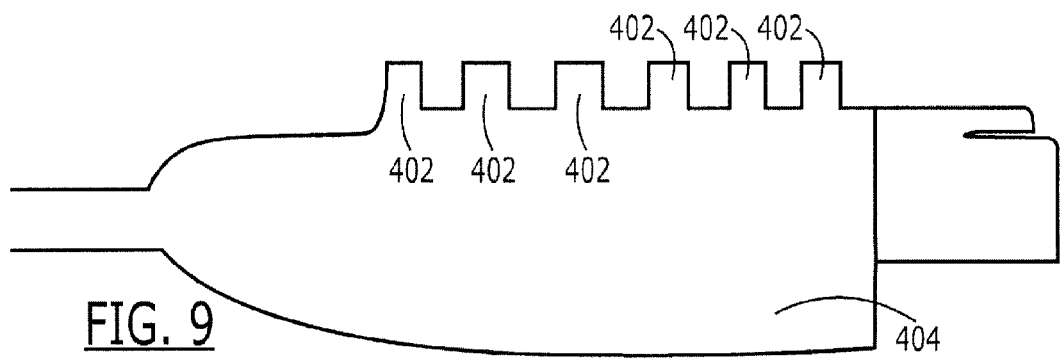
FIG. 9 shows a side view of the tenaculum stabilizer arrangement of FIG. 8.

For example, as shown in FIGS. 6 and 7, an alternative stabilizer arrangement 300 includes a pair of arms 304 extending outward from a portion of a sheath 306 extending distally from a proximal end and including a scope adapter 307 (described in more detail below) to engage finger loops of a tenaculum. Each of the arms 304 is pivotally connected to the sheath 306 at a hinge 308 and biased toward the sheath 306 by a spring 310 so that, after the finger loops of the tenaculum have been passed over ends of the arms 304, the bias of the springs 310 draws the arms 304 into engagement with corresponding braces 312 to lock the tenaculum to the sheath 306. FIGS. 8 and 9 show a stabilizer arrangement 400 according to a further embodiment of the invention including a plurality of projections 402 spaced from one another and extending along the body of a sheath 404 so that a cross bar 406 of a tenaculum 408 can be slid over a desired one of the projections 402 to lock the tenaculum in any of a plurality of desired positions— e.g., to achieve a desired tension. In addition, FIG. 10 shows a stabilizer arrangement 500 according to a further embodiment of the invention including a Velcro strap 502 extending along a portion of the length of a sheath 504 for securing to the sheath a cross bar or other structure of a tenaculum in a desired position relative to the sheath.

The exemplary tenaculum stabilizer arrangement 102 may be connected to a device to be inserted through the cervix in various ways. For example, the stabilizer arrangement 102 may be permanently connected to a sheath handle 110 of the HTA system 100 as an integral component of the HTA system 100 or, alternatively, may be formed as a separate device connected to the sheath handle 110 during preparation for an ablation procedure.

In the exemplary embodiment, the tenaculum stabilizer arrangement 102 is mounted on the sheath handle 110 of the HTA system 100 via a stabilizer track 105 attached to the sheath handle 10 with a sheath 108 extending distally from the handle 110. A stabilizer element 104 includes an elongated rail 106 sliding along the stabilizer track 105 which is significantly shorter than the guide member 22 of the system 10 shown in FIG. 1. The lengths of the rail 106 and the track 105 are selected to, in combination, provide a desired range of motion necessary to accommodate various models of hysteroscope including any accessories such as light and fiber optic bundles of the scope. For example, the distance between the tip of the sheath 120 and the distal end of the stabilizer arrangement 102, or more precisely, a distal end 107 of the stabilizer track 105, is a known constant value short enough to accommodate the shortest scope anticipated. For example, it may be desired to select the lengths of the track 105 and the rail 106 so that, when in a fully extended position, the proximal extension P' of the rail 106 from the handle 110 may be approximately equal to the proximal extension of the guide member 22 of the system 10 of FIG. 1. However, when the stabilizer element 104 and the rail 106 are moved distally from this position, the proximal extension of the rail 106 is reduced compared to that of the guide member 22. Thus, depending on the position of the feature of the tenaculum against which the stabilizer element 104 is to be locked, the extension of the rail 106 may be reduced to permit free rotation of the control handle of even shorter scopes which would be interfered with by the guide member 22 of the system 10 of FIG. 1. Thus, the stabilizer element 104 can be cantilevered out proximally from the proximal end of the rail 106 so that, when the stabilizer element 104 is not in the proximal-most position, the proximal end of the rail 106 does not extend as far proximally as the guide member 22 of the conventional system. As would be understood by those skilled in the art, the track 105 may alternatively be shortened and coupled to a stabilizer element extending proximally therefrom—i.e., with the stabilizer element located proximally of the proximal end of the track 105.

In addition, the stabilizer arrangement 102 may include a mechanism ensuring that the stabilizer element 104 is not inadvertently removed from the track 105. For example, in this embodiment a positive stop 112 formed as a catch protruding from the rail 106 and abutting one or more corresponding abutting features 114, 116 of the track 105. Those skilled in the art will understand that the features 114, 116 may comprise protrusions, detents or other discontinuities in the stabilizer track 105 which engage the positive stop 112 when a desired maximum travel of the stabilizer element 104 in a given direction has been reached. The location of the positive stop 112 is preferably selected to accommodate tenaculums of various dimensions and to permit a desired range of tensioning thereof.

The tenaculum stabilizer arrangement 102 may be manufactured from any of a variety of flexible plastic materials or combinations of such materials. For example, the device may be made of ABS, polyethylene or delrin. In addition, the stabilizer element 104 and/or the stabilizer track 105 may be coated with a low friction material, to ease the sliding movement of the rail 106 on the stabilizer track 105. Those of skill in the art will understand that various other plastic and non-plastic materials may be used in the manufacture of the tenaculum stabilizer device according to the invention.

As shown in FIGS. 4 and 5, an HTA system 200 according to a further embodiment of the invention includes a handle 210 coupled to a proximal end of an HTA sheath 212 with a scope adapter 214 telescoping in and out of a proximal end of the handle 210. The telescoping scope adapter 214 accommodates scopes of various sizes and designs, as described above by extending proximally as needed to support the control handle of the scope and accommodating closely the diameter of the scope. That is, for longer scopes, a significant portion of the length may extend out of the proximal end of the handle 210 and, if left unsupported, this extending portion of the scope may move about in an undesired manner. To prevent this, a user depresses a scope adapter button 216 releasing the adapter 214 from a frame 218 of the handle 210 and slides the adapter 214 until a proximal end of the adapter 214 is separated from the proximal tip of the sheath 212 by a distance selected to enclose a desired portion of the length of the scope. The button 216 is then released to pop outward (e.g., under spring bias) into one of a plurality of locking holes 220, preventing the adapter from moving relative to the handle 210. When in a desired position, the adapter 214 supports the extending portion of the scope (e.g., up to a distal end of the control handle). Furthermore, a scope adapter locking ring 222 may then be rotated to cinch an inner lumen of the adapter 214 around the scope to prevent liquid from passing through the handle 210 and out the proximal end thereof.

Figure 2:
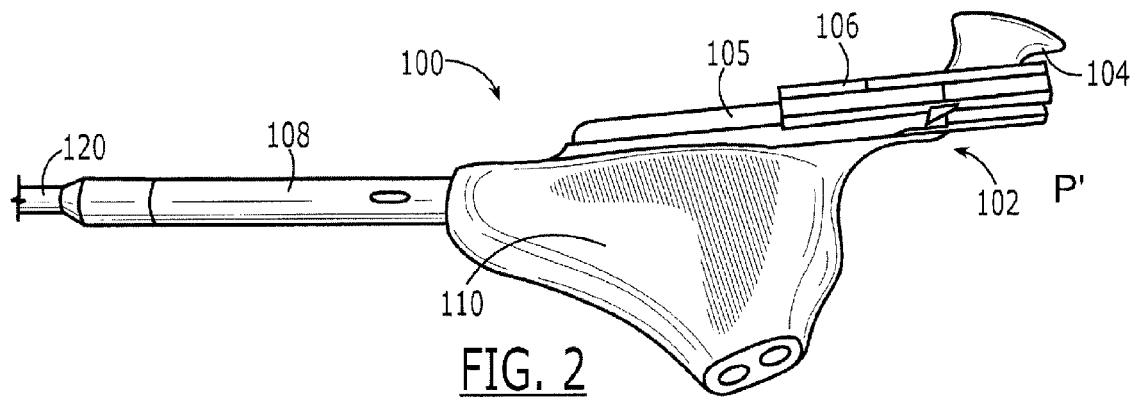
FIG. 2 is a side view of a tenaculum stabilizer according to an embodiment of the present invention.
Figure 3:
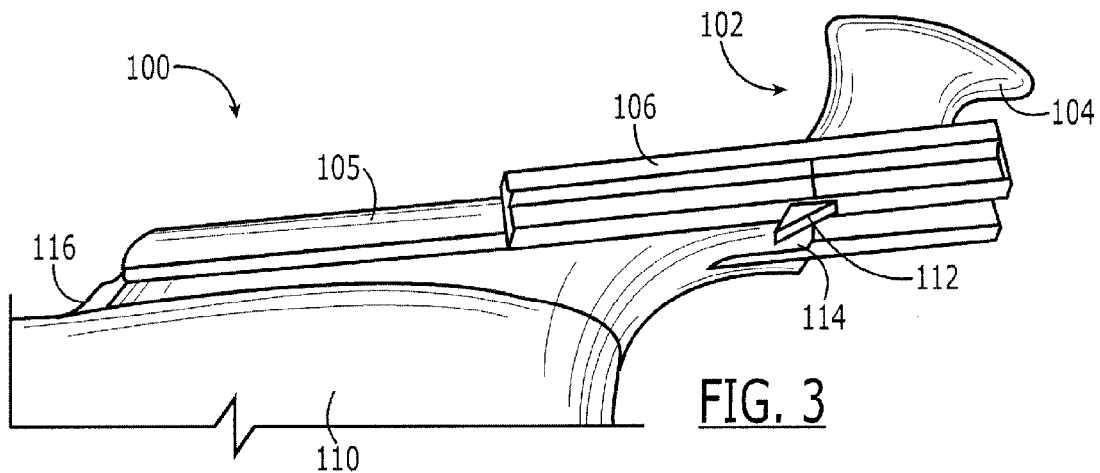
FIG. 3 is a detail view of a positive stop of the tenaculum stabilizer shown in FIG. 2.

Similarly to the embodiments described above, the HTA system 200 includes a tenaculum stabilizer arrangement 230 including a stabilizer element 236 slidably mounted on the handle 210 of the HTA system 200 via a stabilizer track 232 attached to the handle 210. The stabilizer element 236 includes an elongated rail 234 sliding along the stabilizer track 232 which, similar to that of the device of FIGS. 2 and 3, is significantly shorter than the guide member 22 of the system 10 shown in FIG. 1. As with the previously described embodiment, the lengths of the rail 234 and the track 232 are selected to, in combination, provide a desired range of motion necessary to accommodate various models of hysteroscope including any accessories such as light and fiber optic bundles of the scope. For example, the distance between the tip of the sheath 212 and the distal end of the stabilizer arrangement 230, or more precisely, a distal end 238 of the stabilizer track 232, is a known constant value short enough to accommodate the shortest scope anticipated. For example, it may be desired to select lengths of the track 232 and the rail 234 so that, when in a fully extended position, the proximal extension of the rail 234 from the handle 210 may be approximately equal to the proximal extension of the guide member 22 of the system 10 of FIG. 1. However, when the stabilizer element 236 and the rail 234 are moved distally from this position, the proximal extension of the rail 234 is reduced compared to that of the guide member 22. Thus, depending on the position of the feature of the tenaculum against which the stabilizer element 104 is to be locked, the extension of the rail 234 may be reduced to permit free rotation of the control handle of even shorter scopes which would be interfered with by the guide member 22 of the system 10 of FIG. 1.

In addition, the sheath 212 includes, at a distal end thereof, a cervical seal 240 which is formed, for example, as a mesh 242 covered by a sheath of flexible material with a proximal end of the mesh abutting a sleeve 244 which is movable axially within the sheath 212. For example, the sleeve 244 of this embodiment is coupled to a seal actuator 246 which, when rotated relative to the sheath 212 in a first direction moves the sleeve distally to axially compress the mesh 242 and, when rotated in the opposite direction, moves the sleeve proximally. When axially compressed (e.g., between the sleeve 244 and the distal end of the sheath 212), the mesh 242 expands radially away from the sheath 212 to form an expanded distal end of the sheath 212 which may be drawn proximally against the cervical os to enhance the seal of the uterus.

FIG. 11 shows another exemplary embodiment of an HTA system 600 according to the present invention. Similarly to the system 200 described above, the HTA system 600 includes a tenaculum stabilizer arrangement 230 including a stabilizer element 236 slidably mounted on a handle 210 via a stabilizer track 232. The stabilizer element 236 includes an elongated rail 234 sliding along the stabilizer track 232 which, similar to that of the device of FIGS. 2 and 3, is significantly shorter than the guide member 22 of the system 10 shown in FIG. 1. The stabilizer element 236 may be moved along the track 232 by pulling the element 236 proximally allowing a ratcheting surface 270 of the stabilizer element 236 to slide over angled teeth 280 disposed along the track 232. As would be understood by those skilled in the art, distal surfaces of the ratcheting surface 270 and the teeth 280 are preferably both angled substantially parallel to one another extending proximally in a direction away from the track 232 so that the ratcheting surface 270 rides up and over the teeth 280 as the stabilizer element 236 is moved proximally. Distal surfaces of the ratcheting surface 270 and the teeth 280 are preferably substantially perpendicular to a longitudinal axis of the track 232 so that distal movement of the stabilizer element 236 over the track 232 is prevented by contact between the ratcheting surface 270 and the teeth 280. The stabilizer element 236 may be moved distally over the track 232 by bending the stabilizer element 236 proximally, rotating the ratcheting surface 270 out of engagement with the teeth 280. The HTA system 600 also differs from the previously described embodiments in that one or more positive stops (not shown) are located within an internal surface of the rail 234, rather than externally as with the stop 112. The internal positive stop prevents the rail 234 from being removed from the track 232 and similarly to the stop 112, forms a catch which abuts a protruding feature (not shown) located at a proximal and/or a distal end of the track 232 such that movement of the stabilizer element 236 is confined to sliding between the proximal and distal ends of the track 232.

The present invention has been described with reference to specific exemplary embodiments. Those skilled in the art will understand that changes may be made in details, particularly in matters of shape, size, material and arrangement of parts. Accordingly, various modifications and changes may be made to the embodiments. For example, the exemplary devices described may be used to perform ablations of the lining in other bodily cavities or hollow organs other than the uterus. The specifications and drawings are, therefore, to be regarded in an illustrative rather than a restrictive sense.

What is claimed is:

1. An apparatus for treating tissue, comprising:
   a sheath defining a lumen sized and shaped to receive a treatment device therein;
   a guide member comprising a handle coupled to the sheath, a stabilizer track coupled to the handle, and an elongated rail slidably received over the track, the guide member extending a predetermined distance substantially parallel to a longitudinal axis of the sheath; and
   a stabilizer element for engaging an anchoring device coupled to tissue to stabilize the sheath and the treatment device, the stabilizer element being coupled to a proximal portion of the elongated rail, the stabilizer element being movable along the track substantially parallel to the longitudinal axis of the sheath wherein, when in a proximal-most position, a distal end of the stabilizer element is located proximally of a proximal end of the handle.

2. The apparatus of claim 1, wherein the stabilizer track extends distally of a tenaculum engaging surface of the stabilizer element by a distance selected so that, when the stabilizer element is in the proximal-most position, the stabilizer track maintains a portion of its length mounted on the handle sufficient so that force applied from a tenaculum to the stabilizer element prevents undesired movement of the sheath.

3. The apparatus of claim 1, further comprising:
a positive stop limiting relative movement of the stabilizer element and the sheath within a predetermined range.

4. The apparatus of claim 3, wherein the positive stop comprises a first surface discontinuity on the elongated rail with a corresponding surface discontinuity on the stabilizer track.

5. The apparatus of claim 4, wherein the first surface discontinuity includes an abutting surface projecting away from the stabilizer element toward the sheath.

6. The apparatus of claim 1, wherein the stabilizer element is one of fin shaped, hook shaped and groove shaped.

7. The apparatus of claim 1, wherein the stabilizer element is shaped to engage one of a cross bar, a finger loop and a body of a tenaculum.

8. The apparatus of claim 1, further comprising a low friction coating on at least one of the elongated rail and the stabilizer track.

9. The apparatus of claim 1, wherein the stabilizer element is formed of one of ABS, polyethylene and delrin.

10. The apparatus of claim 1, wherein the guide member is integrally formed with the sheath.

11. The apparatus of claim 1, wherein the stabilizer element is lockable in a plurality of positions along the guide member to define a corresponding plurality of positions of the stabilizer element relative to the sheath.

12. The apparatus of claim 1, wherein the guide member and the stabilizer element are dimensioned so that, when the sheath is in a desired position within a body, the stabilizer element may be positioned along the guide member to provide a desired tension to a portion of a tenaculum.

13. The apparatus of claim 1, further comprising a telescoping scope adapter coupled to the handle at a proximal end of the sheath, the handle comprising a depressible button selectively engaging the scope adapter with a respectively formed locking hole in the guide member.

14. The apparatus of claim 13, further comprising a locking ring formed around an inner lumen of the scope adapter to prevent fluid leakage therepast.

* * * * *